US00PP09539P

United States Patent [19]

Zary

[11] Patent Number: Plant 9,539

[45] Date of Patent: May 7, 1996

[54] HYBRID TEA ROSE PLANT NAMED 'JACNOR'

[75] Inventor: Keith W. Zary, Thousand Oaks, Calif.

[73] Assignee: Bear Creek Gardens, Inc., Medford, Oreg.

[21] Appl. No.: 491,142

[22] Filed: Jun. 16, 1995

[51] Int. Cl.[6] ..... A01H 5/00

[52] U.S. Cl. ..... Plt./11

[58] Field of Search ..... Plt./11, 12, 13, Plt./18, 19

*Primary Examiner*—Howard J. Locker

*Attorney, Agent, or Firm*—Klarquist Sparkman Campbell Leigh & Whinston

[57] ABSTRACT

A new and distinct variety of rose plant of the Hybrid Tea class, having an upright, vigorous growth habit; good flower form; large, dark green foliage; and an attractive pink blend flower color.

1 Drawing Sheet

The present invention relates to a new and distinct variety of rose plant of the Hybrid Tea class which was originated by me by crossing the variety JAColite, U.S Plant Pat. No. 4,167, with the variety First Federal's Reinaissance, U.S. Plant Pat. No. 4,459.

The primary objective of this breeding was to produce a new rose variety having the upright, vigorous growth, good flower form and rapid repeat bloom of the female parent combined with the long bud, large foliage and early bloom of the male parent. The objective was substantially achieved, along with other desirable improvements, as evidenced by the following unique combination of characteristics that are outstanding in the new variety and that distinguish it from its parents, as well as from all other varieties of which I am aware:

1. Excellent hybrid exhibition tea flower form.
2. Vigorous, upright growth habit.
3. Attractive rose pink and light pink blend flower color.
4. Large, dark green semi-glossy foliage.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentatge:

*Seed parent.*—JAColite, U.S. Plant Pat. No. 4,167.

*Pollen parent.*—First Federal Renaissance, U.S. Plant Pat. No. 4,459.

Classification:

*Botanical.13 Rosa hybrida.*

*Commercial.*—Hybrid Tea.

FLOWER

Observations made April–November 1994 from specimens grown in a garden environment at Somis, Calif.

Blooming habit: Recurrent.

Bud:

*Size.*—1½–2 inches long when the petals start to unfurl.

*Form.*—Long, pointed ovoid.

*Color.*—When sepals first divide, bud color is Red Group 45C. As the sepals drop and the bud grows, the color becomes Red Group 45C on the petal edges and Red Group 48C to D on the rest of the petal. The upper side of each of the outer petals is Red Group 45C on the petal edges, and Red Group 48C-D on the rest of the petal; the petals at the center of the flower are Red Group 45C; and the lower sides of the petals are Red Group 48C to D, except on the petal edges, where they are Red Group 45C.

*Sepals.*—Color: Green Group 138C, reddish when exposed to direct sun. Surface texture: Covered in fine hairs. There are three normally appendaged sepals. There are two unappendaged sepals with hairy edges.

*Receptacle.*—Color: Green Group 143C. Shape: Funnel. Size: Small (¼"×¼"). Surface: Smooth.

*Peduncle.*—Length: Medium (2½"–3"). Surface: Smooth, with a few glands. Color: Medium green; bronzy where exposed to sunlight. Strength: Stiff, erect.

Bloom:

*Size.*—Large. Average open size is 4½–5 inches.

*Borne.*—Singly.

*Stems.*—Medium length, strong. Average length is about 16–18 inches.

*Form.*—When first open: High centered. Permanence: Retains its form to the end, outer petals curl back.

*Petalage.*—Number of petals under normal conditions: 30–35.

*Color.*—The upper side of the petals is Red Group 45C on the petal edges and Red Group 48C to D elsewhere. The reverse side of the petals is Red Group 48C to D with Red Group 45C on the petal edges. The base of each petal has a greenish-white ¼"×¼" half moon at the point of attachment. The major color on the upper side is Red Group 48C to D.

*Variegations.*—None.

*Discoloration.*—The general tonality at the end of the first day: No change. At the end of the third day: No change.

*Fragrance.*—Moderate.

Petals:

*Texture.*—Thick and leathery.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: Long (7 days). As a cut flower: Long (8–9 days).

Reproductive parts:

*Anthers.*—Size: Medium. Quantity: Many. Color: Yellow. Arrangement: Regular around styles.

*Filaments.*—Color: Yellow with red at their base.

*Pollen.*—Color: Lemon yellow.

*Styles.*—Color: Red.

*Stigmas.*—Color: Greenish-white.

Form: Bush.

Growth: Vigorous; plant at maturity (one year without pruning) is 5 feet in height and 4 feet in width.

Foliage:

*Number of leaflets on normal mid-stem leaves.*— 5, 6 or 7.

*Size.*—Large (6½"–5").

*Quantity.*—Normal.

*Color.*—New foliage: Greyed Red 178B. Old Foliage: Upper surface: Green Group 137A. Lower surface: Green Group 137C.

Leaflets:

*Shape.*—Pointed oval.

*Texture.*—Upper side: Leathery, glossy.

*Edge.*—Serrated.

*Serration.*—Single and small.

*Petiole rachis.*—Color: Green.

*Petiole underside.*—Smooth, with occasional prickles.

*Stipules.*—Medium (½"), serrated and bearded.

*Disease resistance.*—Resistant to mildew, but susceptible to rust, under normal growing conditions at Somis, Calif.

Wood:

*New wood.*—Color: Reddish, but becoming light green quickly. Bark: Smooth.

*Old wood.*—Color: Green. Bark: Smooth.

Prickles:

*Quantity.*—On main canes from base: Ordinary. On laterals from main canes: Ordinary.

*Form.*—Medium (5/16"), hooked downward.

*Color when young.*—Red.

Small prickles:

*Quantity.*—On main stalks: Few. On laterals: Few.

*Color.*—Brown.

I claim:

1. A new and distinct variety of rose plant of the Hybrid Tea class, substantially as herein shown and described, characterized particularly as to novelty by the unique combination of its vigorous, upright growth habit; its large, dark green foliage; its attractive pink blend flower color; and its excellent, high-centered exhibition flower form.

* * * * *

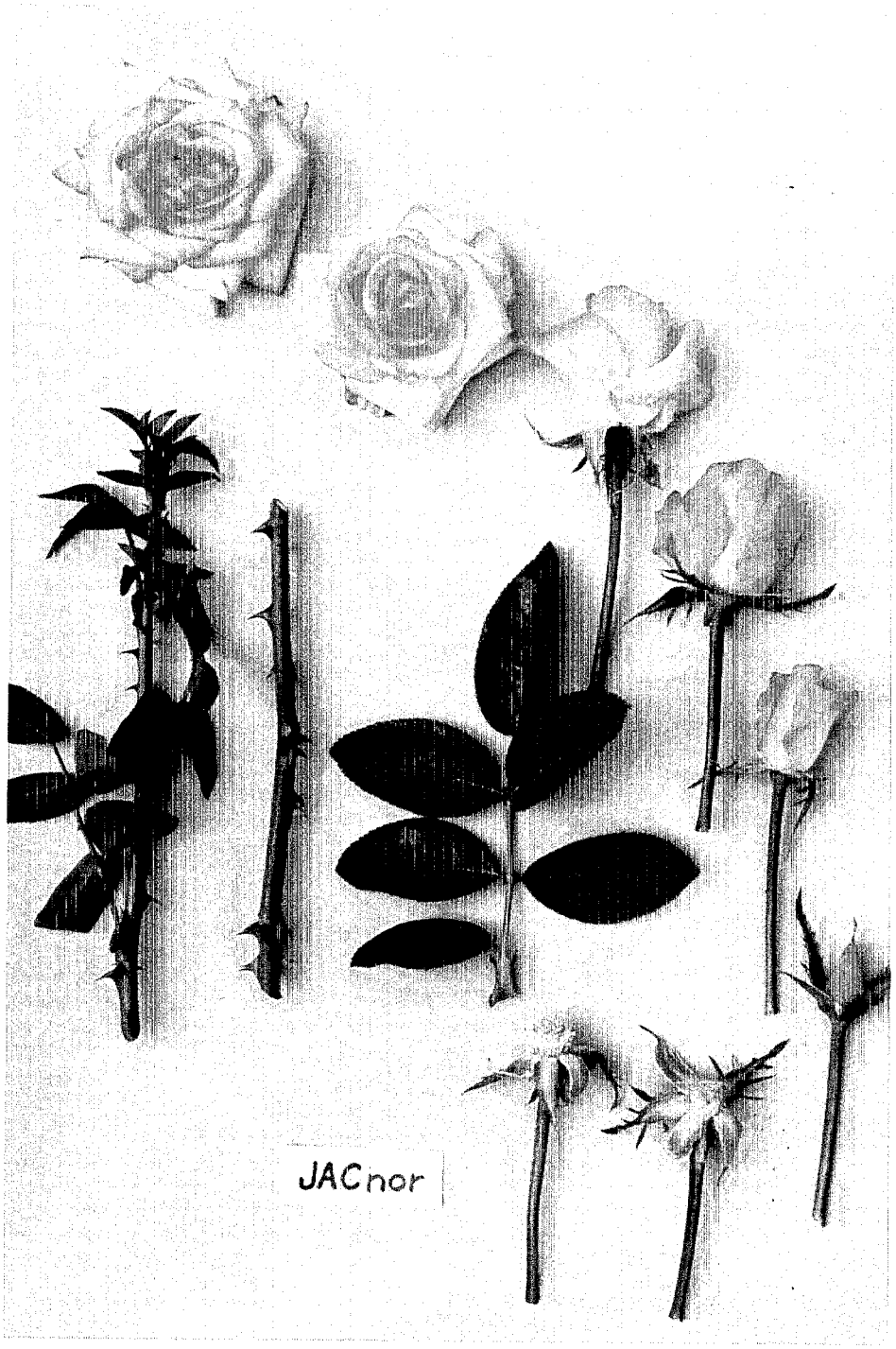
JACnor

UNITED STATES PATENT AND TRADEMARK OFFICE

CERTIFICATE OF CORRECTION

PATENT NO. : PP 9,539

DATED : May 7, 1996

INVENTOR(S) : Keith W. Zary

It is certified that error appears in the above-indentified patent and that said Letters Patent is hereby corrected as shown below:

Column 1, line 4, "Reinaissance" should read --Renaissance--.

Column 1, line 34, "Parentatge" should read --Parentage--.

Column 1, line 40, "Botanical.13 Rosa" should read --Botanical: Rosa--.

Column 3, line 14, "6½" - 5" should read --6½" x 5"--.

Signed and Sealed this

Fifteenth Day of October, 1996

*Attest:*

*Attesting Officer*

BRUCE LEHMAN

*Commissioner of Patents and Trademarks*